United States Patent
Lien

(10) Patent No.: US 9,162,781 B2
(45) Date of Patent: *Oct. 20, 2015

(54) EASY-OPEN PROTECTIVE PACKAGE FOR ASEPTIC PRESENTATION

(71) Applicant: AVENT, INC., Alpharetta, GA (US)

(72) Inventor: Khoa T. Lien, Milton, GA (US)

(73) Assignee: Avent, Inc., Alpharetta, GA (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/955,509

(22) Filed: Jul. 31, 2013

(65) Prior Publication Data

US 2015/0033673 A1    Feb. 5, 2015

(51) Int. Cl.
| | | |
|---|---|---|
| *B65B 11/00* | (2006.01) | |
| *A61F 15/00* | (2006.01) | |
| *B65B 67/08* | (2006.01) | |
| *A61B 19/04* | (2006.01) | |

(52) U.S. Cl.
CPC ............. *B65B 11/004* (2013.01); *A61B 19/045* (2013.01); *A61F 15/001* (2013.01); *B65B 67/08* (2013.01)

(58) Field of Classification Search
CPC ........ B65B 55/02; B65B 55/04; B65B 55/00; B65B 11/004; B65B 67/08; A61L 2/00; A61F 15/001
See application file for complete search history.

(56) References Cited

U.S. PATENT DOCUMENTS

| | | | |
|---|---|---|---|
| 3,107,786 A * | 10/1963 | Adelman | 206/278 |
| 3,181,695 A * | 5/1965 | Taterka et al. | 206/299 |
| 3,225,920 A * | 12/1965 | Reilly | 206/299 |
| 3,338,992 A | 8/1967 | Kinney | |
| 3,341,394 A | 9/1967 | Kinney | |
| 3,392,503 A * | 7/1968 | Vaughan | 53/461 |
| 3,502,763 A | 3/1970 | Hartmann | |
| 3,542,019 A * | 11/1970 | Gittins | 128/855 |
| 3,542,615 A | 11/1970 | Dobo et al. | |
| 3,692,618 A | 9/1972 | Dorschner et al. | |
| 3,780,857 A * | 12/1973 | Rosano et al. | 206/370 |
| 3,802,817 A | 4/1974 | Matsuki et al. | |
| 3,849,241 A | 11/1974 | Butin et al. | |
| 4,340,563 A | 7/1982 | Appel et al. | |
| 4,342,392 A * | 8/1982 | Cox | 206/438 |
| 4,705,171 A | 11/1987 | Eldridge | |
| 4,754,914 A * | 7/1988 | Wischusen, III | 229/87.08 |
| 5,057,368 A | 10/1991 | Largman et al. | |
| 5,069,970 A | 12/1991 | Largman et al. | |
| 5,277,976 A | 1/1994 | Hogle et al. | |
| 5,466,410 A | 11/1995 | Hills | |
| 5,479,761 A * | 1/1996 | Weder | 53/461 |
| 5,635,134 A | 6/1997 | Bourne et al. | |
| 6,151,869 A * | 11/2000 | Weder | 53/461 |
| 6,406,764 B2 | 6/2002 | Bayer | |
| 7,560,082 B2 | 7/2009 | Stecklein et al. | |
| 7,922,983 B2 | 4/2011 | Prokash et al. | |
| 2006/0104856 A1* | 5/2006 | Farrell et al. | 422/1 |

FOREIGN PATENT DOCUMENTS

| | | |
|---|---|---|
| CH | 437115 | 5/1967 |
| GB | 2 252 910 A | 8/1992 |

OTHER PUBLICATIONS

Search Report and Written Opinion for PCT/IB2014/063234 dated Nov. 3, 2014, 9 pages.

* cited by examiner

*Primary Examiner* — Regina M Yoo

(74) *Attorney, Agent, or Firm* — Dority & Manning, P.A.

(57) ABSTRACT

The present disclosure describes a procedure for wrapping an item to be sterilized with a protective sheet in such a way as to allow a rapid unwrapping of the item for use. This procedure saves time in unwrapping and reduces the risk of loss of sterility of the item and stress on medical personnel.

10 Claims, 5 Drawing Sheets

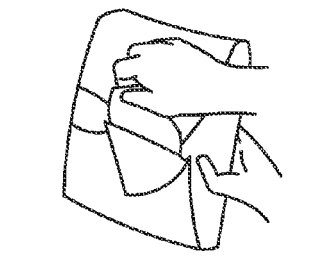
FIG. 1a (PRIOR ART)
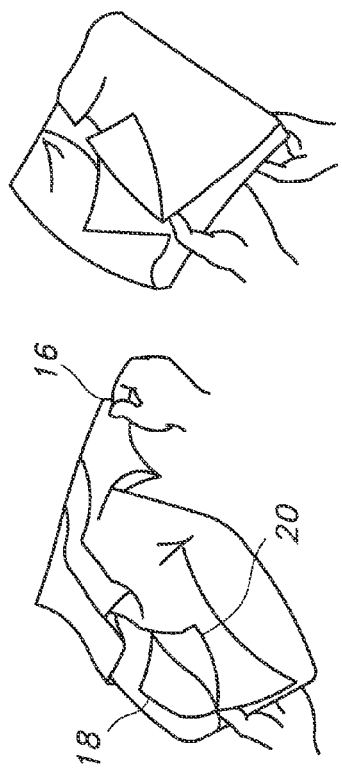
FIG. 1b (PRIOR ART)
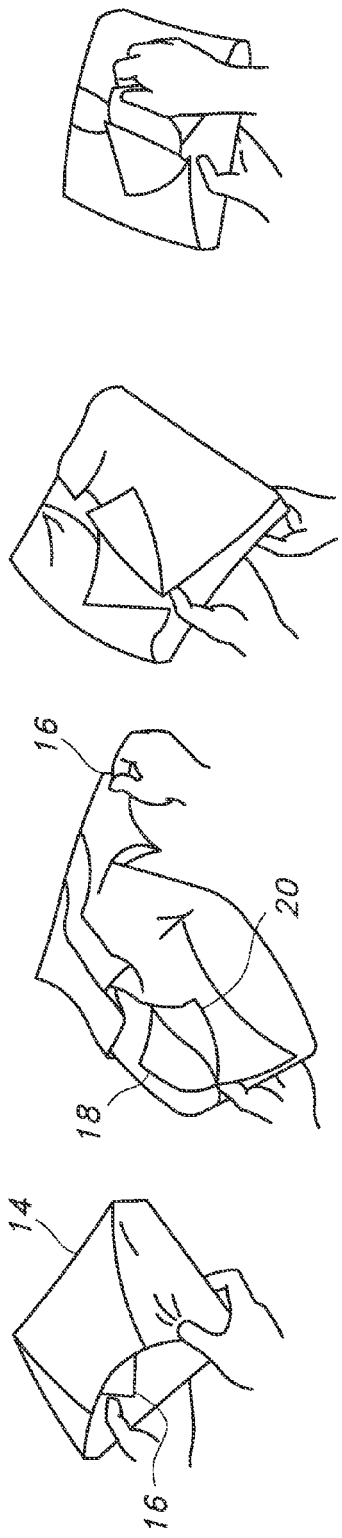
FIG. 1c (PRIOR ART)
FIG. 1d (PRIOR ART)
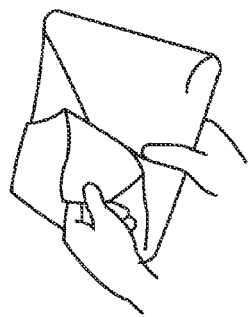
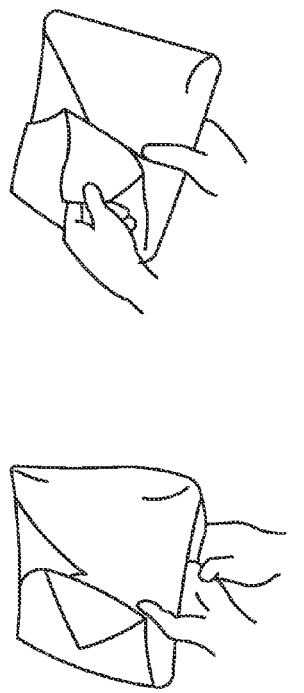
FIG. 1e (PRIOR ART)
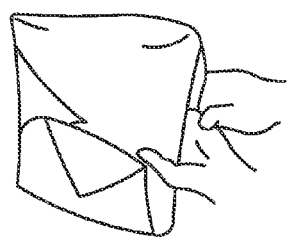
FIG. 1f (PRIOR ART)
FIG. 1g (PRIOR ART)

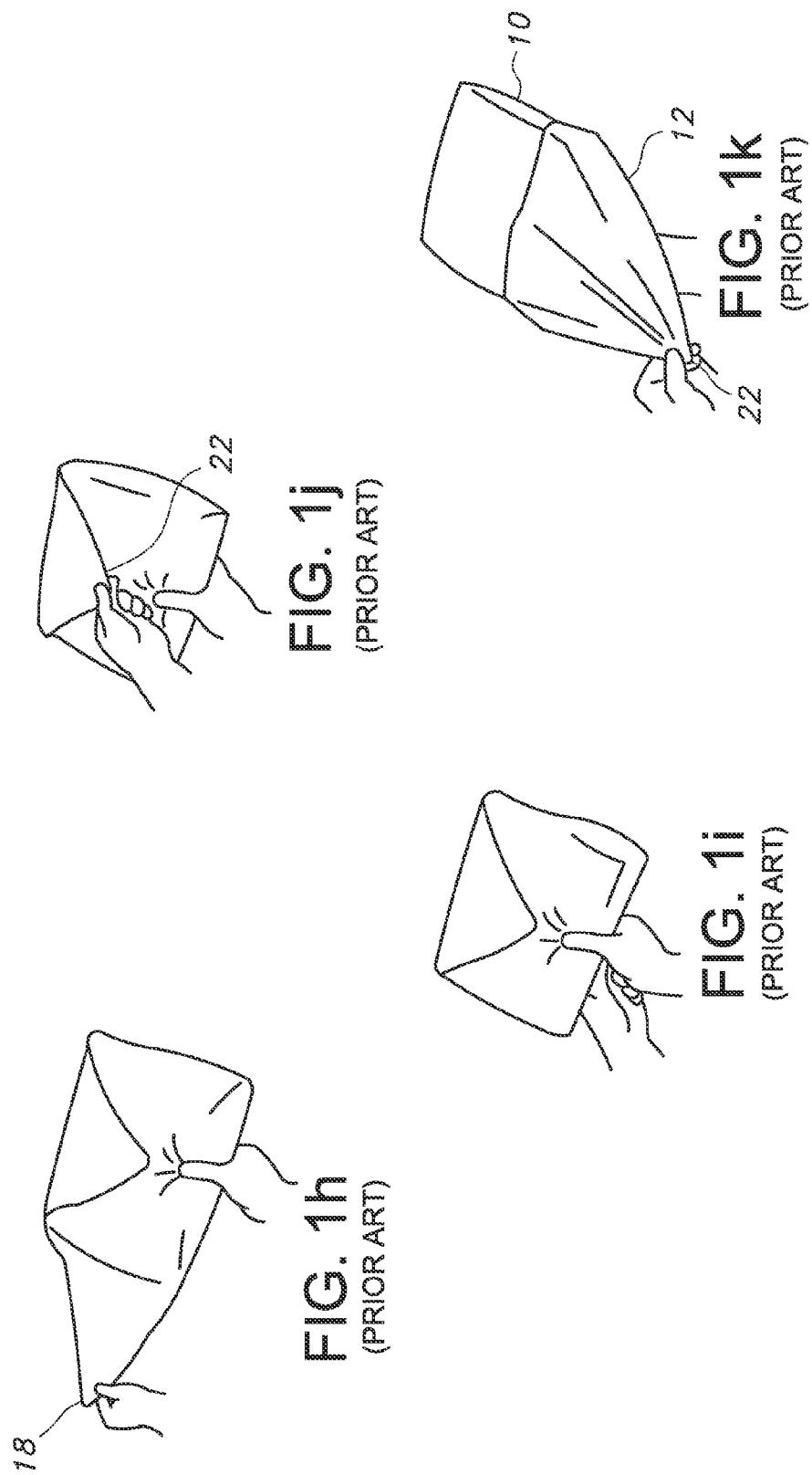

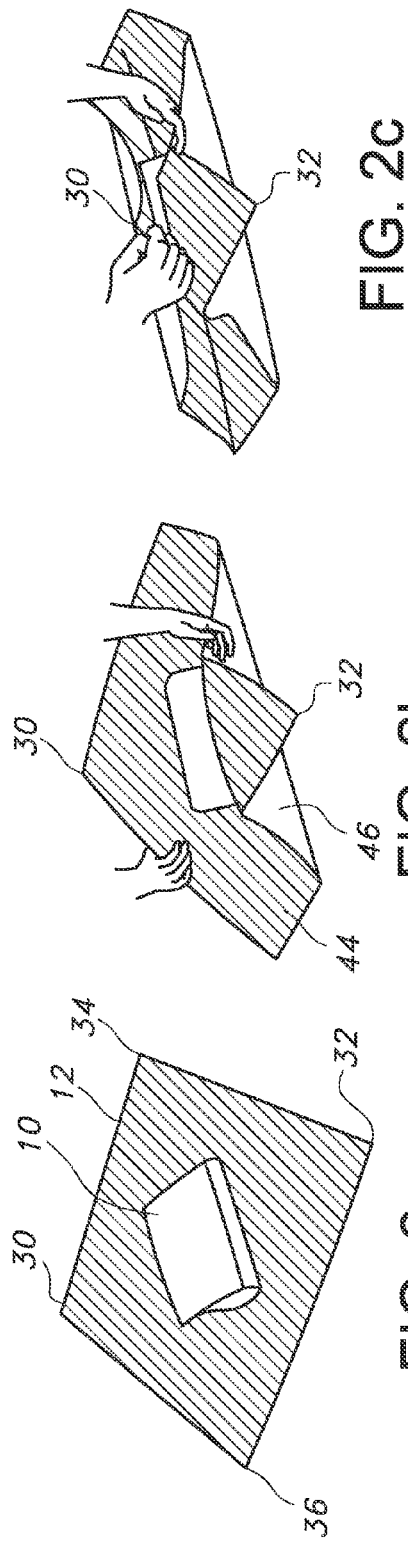
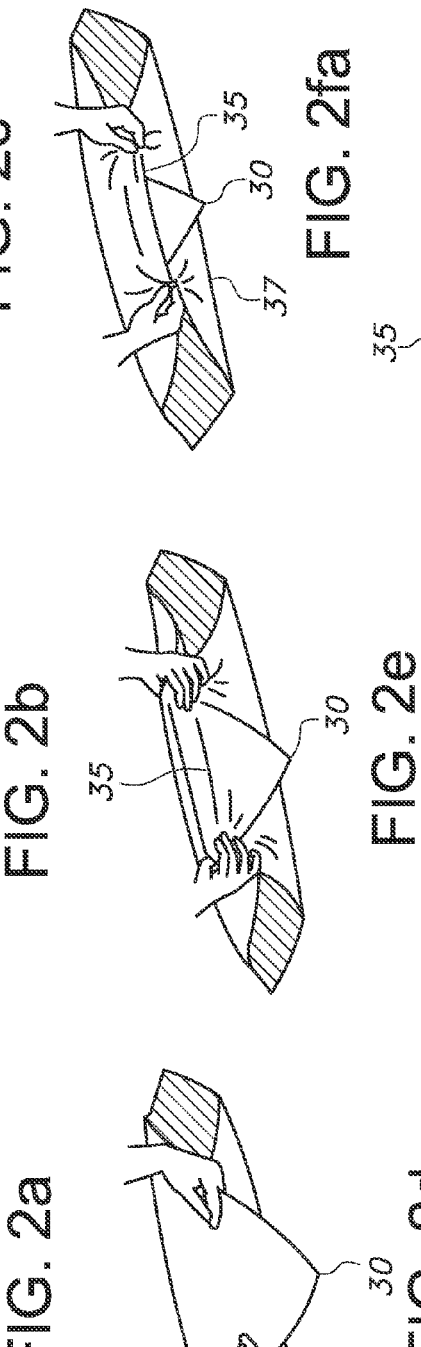
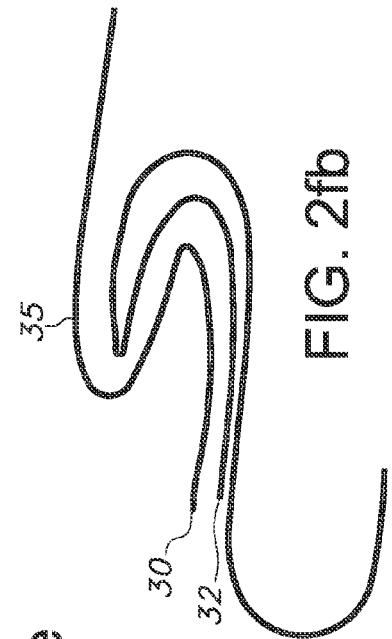

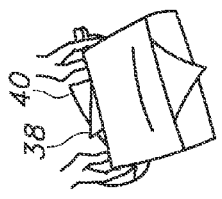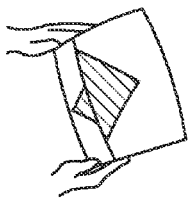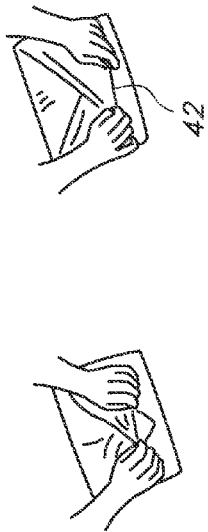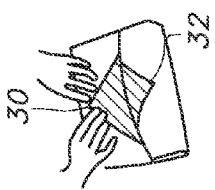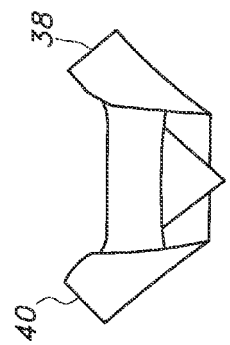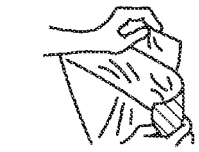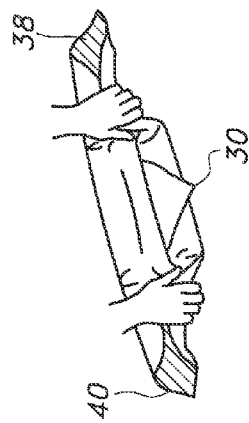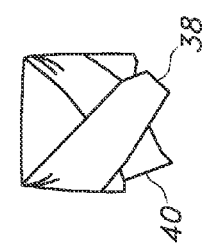

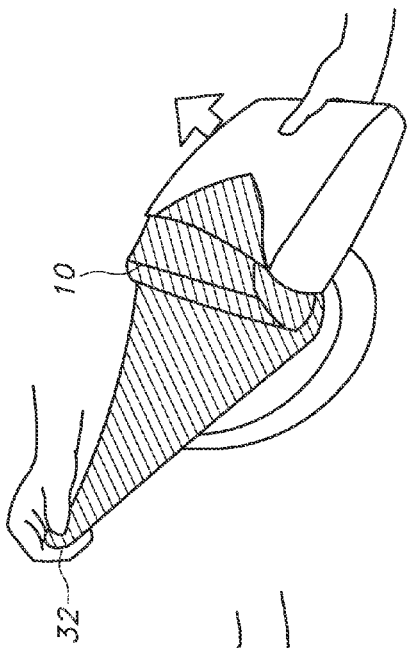
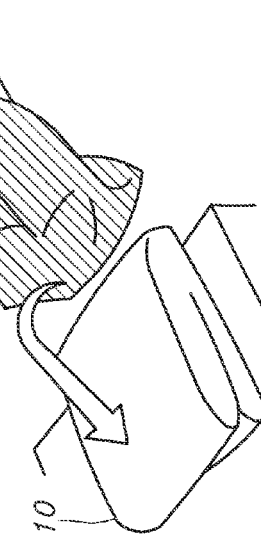
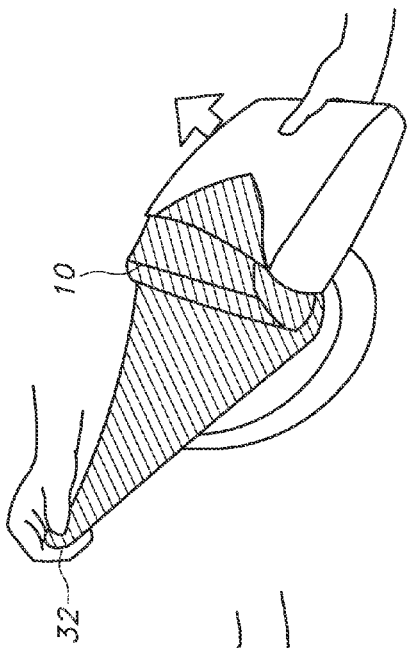
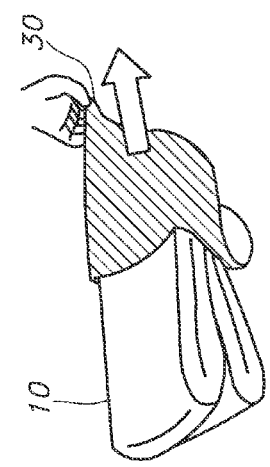
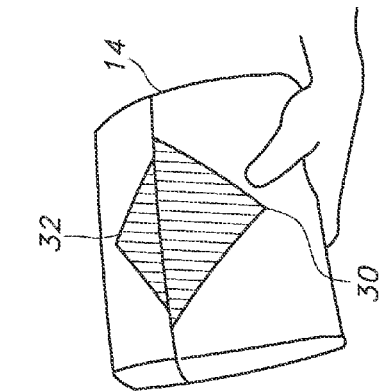
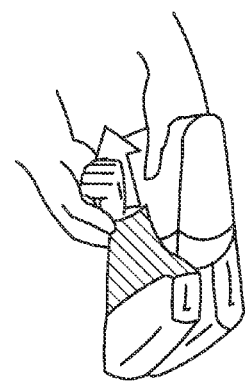

EASY-OPEN PROTECTIVE PACKAGE FOR ASEPTIC PRESENTATION

BACKGROUND

The present disclosure relates to a packaging system for protection and aseptic presentation of sterilized items. One use of the invention is for protecting and aseptically presenting folded sterile protective garments such as surgical gowns.

Protective garments, such as coveralls and gowns, designed to provide barrier protection to a wearer are well known in the art. Such protective garments are used in situations where isolation of a wearer from a particular environment is desirable, or it is desirable to inhibit or retard the passage of hazardous liquids and biological contaminates through the garment to the wearer.

In the medical and health-care industry, particularly with surgical procedures, a primary concern is isolation of the medical practitioner from patient fluids such as blood, saliva, perspiration, etc. In addition, surgical gowns must be sterile for use to protect the patient from infection.

Surgical gowns are normally packaged by the manufacturer within a protective sheet within which the gown may be sterilized. Appropriate protective sheets include those as shown, for example, in U.S. Pat. No. 5,635,134 to Bourne, et al. which discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, US patent publication 2001/0036519 by Robert T. Bayer discloses a two ply sterilization wrap that is formed of a single sheet of protective sheet material which is folded to form two similarly sized, superposed panels that are bonded to each other. As yet another example, US patent publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency. Sterilization wraps may also have a single ply only and these are suitable for use with the invention. Sterilization wraps are commonly made from non-woven materials made by the spunbonding and meltblowing processes.

Once sterilized, the gown must be removed from the protective sheet for use. This removal procedure can be quite complicated, involving numerous steps that must be performed in a fashion that maintains the sterility of the gown. FIG. 1 shows an eleven step procedure for the removal of a gown from its packaging and will be discussed in greater detail below. This prior art procedure takes quite some time and must be performed properly to maintain the sterility of the gown. If the sterility of the gown is lost, the gown must be discarded and another opened, obviously raising costs.

A procedure for packaging an article, e.g., a folded surgical gown, so that it may be unwrapped and removed from its packaging more quickly, i.e. with fewer steps, and with less risk of compromising the sterility of the article would help reduce costs and reduce stress for medical personnel.

SUMMARY

The present disclosure describes a packaging system and a procedure for use of the system for protecting and presenting an item, e.g. a surgical gown that has been sterilized within the packaging system. This procedure reduces the number of steps required for unwrapping. This procedure saves time in unwrapping and reduces the risk of loss of sterility of the item and stress on medical personnel.

The procedure includes at least the steps of:
a) providing a sheet, the sheet having north, south, east and west corners, and east and west sides,
b) placing an item on an upper surface of the sheet,
c) folding the south corner of the sheet up over the item and then folding it back on itself,
d) folding the north corner over the item and then folding an overlapped portion of the north and south corners together to create a pleat with the north corner exposed and overlapping the south corner, the pleat spanning the item and item sides,
e) gathering the sheet on the east side and the west side of the item at an angle and folding the sheet under the item so the east and west sheet cross,
f) securing the east and west sides on the back of the package.

Other objects, advantages and applications of the present disclosure will be made clear by the following detailed description of a preferred embodiment of the disclosure and the accompanying drawings wherein reference numerals refer to like or equivalent structures.

BRIEF DESCRIPTION OF THE DRAWINGS

FIGs. 1a through 1k represent a series of drawings of the prior art steps of unwrapping a sterile item, as exemplified by a folded gown.

FIGs. 2a through 2p represent the unique folding technique disclosed herein. Specifically, FIGs. 2a through 2p show the steps for wrapping an item, as exemplified by a folded gown.

FIGs. 3a through 3f represent the steps of unwrapping a sterile item that has been wrapped according to the procedure shown in FIGs. 2a throught 2p.

DETAILED DESCRIPTION

Reference will now be made to the drawings in which the various elements of the present disclosure will be given numeral designations and in which the disclosure will be discussed so as to enable one skilled in the art to make and use the disclosure. It is to be understood that the following description is only exemplary of the principles of the present disclosure, and should not be viewed as narrowing the pending claims. Those skilled in the art will appreciate that aspects of the various embodiments discussed may be interchanged and modified without departing from the scope and spirit of the disclosure.

FIG. 1 is a series of drawings (a through k) of the prior art steps of aseptically unwrapping a sheet package from around a folded gown. In FIG. 1a the wrapped gown 14 is held in the hands with an exposed corner 16 pointing at the user. The exposed corner is peeled upwardly away from the user (FIG. 1b) to expose two opposite corners 18, 20 folded facing away from each other. The part peeled away from the user is folded under the package (FIG. 1c). The right hand corner 20 exposed in FIG. 1b is pulled to the right (FIG. 1d and e) and folded under the package (FIG. 1f). The left hand corner 18 exposed in FIG. 1b is pulled to the left (FIG. 1g and h) and folded under the package (FIG. 1i). The remaining corner 22 is pulled towards the user (FIG. 1j) to reveal the gown 10 (FIG. 1k) that may then be deposited on a sterile surface for use, completely free of the wrap 12.

The disclosed procedure of wrapping an item, such as a gown, produces a package that may be opened with far fewer steps than that of the prior art. It should be noted that the procedure below is comprehensive and that some steps may be eliminated (e.g. the final presentation step) as will be obvious to those skilled in the art. For ease of understanding the surfaces of the sheet in FIG. 2 are different shades or colors, though an actual sheet may have different or the same colors on each side.

The steps of folding are subsequently further described with, as an illustrative item, a gown that is folded into a generalized prism shape having top and bottom faces and four relatively thin sides. The steps include:

1) laying out the sheet 12 unfolded and flat, the sheet having north, south, east and west corners (30, 32, 34, 36 respectively) as indicated in FIG. 2*a*, with the lower surface 46 of the sheet on a flat surface,
2) desirably centrally placing the gown 10 so a face of the gown is on the upper surface 44 of the sheet and desirably oriented so that the north, south, east and west sides of the gown point towards respective corners of the sheet (FIG. 2*a*),
3) folding up the south corner of the sheet over the gown to at least partially cover the exposed surface of the gown so that the upper surface of the sheet that is closest to the gown is desirably in close proximity to or directly contacts the south side of the gown and then folding the south corner back on itself on top of the gown (FIG. 2*b*) to form a first ply over a second ply,
4) folding the north corner as a third ply over the gown and over the south corner of the sheet (FIG. 2*c* and *d*),
5) pinching a portion of the overlapped third and first plys of the north corner and south corners (FIG. 2*e*) to create a four ply pleat 35 that spans completely across the upper surface and sides of the gown, and laying the pleat down in the south direction (FIG. 2*fa* and pleat cross-section FIG. 2*fb*) (note that the front edge 37 of the package does not have folds),
6) gathering the southernmost portions of the sheet on the east and west sides 38, 40 that are near two opposing sides of the gown (FIG. 2*ga*) and folding them towards the north so that they fold at an angle to either side of the gown (FIG. 2*gb*) to cover the pleat in order to form a "wing", (note, the wings should not fold over the gown)
7) folding the gathered "wings" (i.e., the sides 38, 40) under the package as indicated by the arrows in FIG. 2*h* so that they are fully under the gown and they cross (overlap) (FIG. 2*i*),
8) turning the partially wrapped package over or upside down (FIG. 2*j*) so that the back of the package is exposed (faces up),
9) securing the east and west sides on the back of the package, for example, by tucking the east and west corners (34, 36) under the folded wings to create a fold 42 (FIGS. 2*k*, 2*l* and 2*m*),
10) turning the package over or right side up (FIG. 2*n*),
11) folding down the north corner 30 to expose the south corner 32 (FIG. 2*o*),
12) presenting the finished package (FIG. 2*p*) by turning it around with the north and south corners accessible (exposed) for manipulation. This provides a package 14, with the gown 10 securely located
13) inside and isolated from the external environment by the sheet and the folds of the sheet.

After completion of the folding steps to form the package 14, the package is ready for sterilization using a sterilant that passes through the sheet, e.g., steam, gaseous ethylene oxide. After sterilization, the isolated contents, e.g., gown 10, and the interior surfaces of the sheet are kept in a sterile condition by the barrier properties of the sheet until the package is opened. The folds of the package facilitate aseptic opening.

By "aseptic opening" is meant that unfolded surfaces of the package do not pass over the contents of the package during the process of opening. This ensures that the inner sterilized surfaces of the package always fold away from the contents.

The package is easily opened aseptically by holding the package in one hand with the north corner pointing towards the user (desirably the user holds the north corner so that the north corner remains pointing at the user), pulling the south corner (the smaller corner in FIG. 2*p*) away from the user and desirably under and around the package towards the north corner, making the contents immediately available for use. In order to maintain an aseptic presentation, the north corner should remain in place on top of the package so that it does not touch the contents of the package or the item.

The package may also be opened aseptically by laying the package on a surface and simultaneously pulling the north and south corners in opposite directions to unfold the wrapped sheet and expose the sterile item.

FIG. 3 is a series of drawings (a through f) of the steps of unwrapping a folded gown that has been wrapped according to this disclosure. In FIG. 3*a* the package 14 is held in the hands with two exposed corners, the smaller one (the south corner 32) pointing away from the user. The smaller exposed corner is peeled away from the user (FIG. 3*b*) and folded under the package (FIG. 3*c*). The larger exposed corner (the north corner 30) is then pulled towards the user (FIG. 3*d*) to expose the gown 10 (FIG. 3*e*) so that it may then be deposited on a sterile surface, completely free of the sheet (FIG. 3*f*) or presented for use.

The sheet used in the packaging procedure disclosed herein is shown in the drawings as approximately square for ease of illustration. This is not meant to be limiting since in actual practice the sheet may be square, rectangular, diamond or of another shape. In addition, though the terminology herein has referred to "gowns" for ease of discussion, the item, article or contents wrapped using the disclosed procedure may be, for example, a kit containing medical instruments, a medical device, or virtually anything that may be wrapped and sterilized, and is not meant to limit the disclosure to "gowns".

Sterilization commonly occurs by a sterilant penetrating through the package. In order to remain sterile after sterilization, the item must be completely covered by the sterilization sheet during and after sterilization. Incomplete coverage of the item by the sheet would allow infiltration of biological materials and so render the item unsterile.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802, 817 to Matsuki et al., U.S. Pat. Nos. 3,338,992 and 3,341,394 to Kinney, U.S. Pat. No. 3,502,763 to Hartman, and U.S. Pat.

No. 3,542,615 to Dobo et al. Spunbond fibers are generally not tacky when they are deposited onto a collecting sheet. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting sheet to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting sheet.

EXAMPLES

Example 1

A gown was folded into a generally prism shape with two opposing face dimensions of about 10 inches by 8 inches (25.4 by 20.3 cm) and four sides separating the faces by about 2 inches (5 cm). This folded gown was centrally placed on a square sterilization wrap sheet of about 24×24 inches (61 by 61 cm). When folded in accordance with the described procedure, the sheet covered the item completely with the pleat on top of the item approximately in the center of the item. The pleat extended across the long dimension of the item and substantially beyond. When the wings were folded under the item, no open area was visible on either side of the item. The item was easily unwrapped.

Comparative Example 1

A gown was folded into a generally prism shape with two opposing face dimensions of about 10 inches by 8 inches (25.4 by 20.3 cm) and four sides separating the faces by about 2 inches (5 cm). This folded gown was centrally placed on a square sterilization wrap sheet of about 20×20 inches (51 by 1 cm). When folded in accordance with the described procedure, the pleat did not extend fully across the longest dimension of the item. When the wings were folded under the item, open area was visible on either side of the item, which is unacceptable, making this size sheet unsuitable for this size item.

Comparative Example 2

A gown was folded into a generally prism shape with two opposing face dimensions of about 10 inches by 8 inches (25.4 by 20.3 cm) and four sides separating the faces by about 2 inches (5 cm). This folded gown was placed off-center about one third of the distance from the east corner on a square sterilization wrap sheet of about 24×24 inches (61 by 61 cm). When folded in accordance with the described procedure, with the pleat on top of the item approximately in the center of the item, but with a gap in the coverage visible on the west side of the item because of the off-center placement of the item on the sheet. The pleat extended across the long dimension of the item and substantially beyond on the east side.

When the wings were folded under the item, open area was visible on the west side of the item, making this placement of the item on the sheet unsuitable.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A procedure of packaging an item into a package comprising the steps of:
   a) providing a sheet, the sheet having north, south, east and west corners, and east and west sides,
   b) placing the item having a front and back on an upper surface of the sheet,
   c) folding the south corner of the sheet up over the tem and then folding it back on itself,
   d) folding the north corner over the item and then folding an overlapped portion of the north and south corners together to create a pleat with the north corner exposed and overlapping the south corner, said pleat spanning the item and item sides,
   e) gathering the sheet on the east side and the west side of the item at an angle and folding the sheet under the item so the east and west side cross, and
   f) securing the east and west sides on the back of the package.

2. The procedure of claim I further comprising the step of folding down the north corner to expose the south corner.

3. The procedure of claim I further comprising the step of turning the package over after securing the east and west sides on the back of the package.

4. The procedure of claim 3 further comprising the step of turning the package over after securing the east and west sides on the back of the package by folding the east and west sides together, one under the other, to create a neat fold.

5. The procedure of claim 1 wherein the item is selected from the group consisting of gowns, drapes, medical kits, and medical devices.

6. The procedure of claim 1 wherein the item is sterilized by a sterilant penetrating through the package.

7. A package formed from an item and encasing sheet according to the procedure of claim 6.

8. The package of claim 7 wherein the sterilized item remains sterile until the package is opened.

9. The package of claim 7 wherein the item is selected from the group consisting of gowns, drapes, medical kits, and medical devices.

10. A method of aspectically presenting the item contained within the package of claim 7.

* * * * *